(12) United States Patent
Misle et al.

(10) Patent No.: US 10,569,027 B2
(45) Date of Patent: Feb. 25, 2020

(54) EPIDURAL NEEDLE ASSEMBLY

(71) Applicants: Gayle Misle, Millbrae, CA (US); Ryan C. Patterson, Farmington, UT (US); Trent J. Perry, Kaysville, UT (US)

(72) Inventors: Gayle Misle, Millbrae, CA (US); Ryan C. Patterson, Farmington, UT (US); Trent J. Perry, Kaysville, UT (US)

( * ) Notice: Subject to any disclaimer, the term of this patent is extended or adjusted under 35 U.S.C. 154(b) by 29 days.

(21) Appl. No.: 15/354,249

(22) Filed: Nov. 17, 2016

(65) Prior Publication Data

US 2017/0304555 A1    Oct. 26, 2017

Related U.S. Application Data

(63) Continuation-in-part of application No. 15/133,660, filed on Apr. 20, 2016, now Pat. No. 10,028,768.

(51) Int. Cl.
*A61M 5/32* (2006.01)
*A61M 5/34* (2006.01)

(52) U.S. Cl.
CPC ............ *A61M 5/32* (2013.01); *A61M 5/3287* (2013.01); *A61M 5/3297* (2013.01); *A61M 5/34* (2013.01); *A61M 2005/3201* (2013.01)

(58) Field of Classification Search
CPC ...... A61M 5/32; A61M 5/321; A61M 5/3213; A61M 5/3243; A61M 5/3271; A61M 25/0612; A61M 25/0625; A61M 2005/3201; A61M 25/065; A61M 25/0606; A61M 25/06; A61M 2025/0687; A61M 2005/1585; A61M 5/3297; A61B 2017/348; A61B 17/34
See application file for complete search history.

(56) References Cited

U.S. PATENT DOCUMENTS 2,919,692 A    1/1960  Ackermann
5,352,205 A *  10/1994 Dales ................ A61M 25/0606
                                                604/158
5,505,711 A *  4/1996  Arakawa ........... A61M 25/0637
                                                604/171
5,817,060 A *  10/1998 Overton .................. A61M 5/50
                                                604/164.01

(Continued)

FOREIGN PATENT DOCUMENTS

WO    WO-2015015127 A2 *  2/2015  .......... A61M 25/065

*Primary Examiner* — Kevin C Sirmons
*Assistant Examiner* — Tezita Z Watts
(74) *Attorney, Agent, or Firm* — Dennis L. Thomte; Thomte Patent Law Office LLC

(57) ABSTRACT

An epidural needle assembly including an epidural needle assembly and an injection needle assembly. The injection needle assembly is slidably mounted on the needle of the epidural needle assembly between extended and retracted positions. The injection needle assembly includes an injection hub having an injection needle secured thereto which extends forwardly therefrom. When the injection needle assembly is in its retracted position, the forward end of the injection needle is positioned rearwardly of the forward end of the epidural needle. When the injection needle assembly is in its extended position, the forward end of the injection needle is positioned forwardly of the forward end of the epidural needle. When in its extended position, the injection needle is able to create a hole in the skin of a person or animal to permit the epidural needle to be inserted therein.

2 Claims, 8 Drawing Sheets

(56) References Cited

U.S. PATENT DOCUMENTS

| | | | | |
|---|---|---|---|---|
| 5,871,060 A | * | 2/1999 | Jensen | E21B 10/5673 |
| | | | | 175/420.2 |
| 2006/0106348 A1 | * | 5/2006 | Lichtenberg | A61M 25/0631 |
| | | | | 604/164.08 |
| 2008/0243092 A1 | * | 10/2008 | Nilsson | A61M 25/0606 |
| | | | | 604/272 |
| 2009/0054866 A1 | | 2/2009 | Teisen-Simony et al. | |

\* cited by examiner

EPIDURAL NEEDLE ASSEMBLY

CROSS REFERENCE TO RELATED APPLICATION

This is a Continuation-In-Part Application of application Ser. No. 15/133,660 filed Apr. 20, 2016, entitled CANNULA AND NEEDLE ASSEMBLY.

BACKGROUND OF THE INVENTION

Field of the Invention

This invention relates to an epidural needle assembly and more particularly to an injection needle assembly to enable an epidural needle to be inserted into various parts of a person such as knees, arms, shoulders, back, etc., or into an animal.

Description of the Related Art

An epidural needle is a needle usually used in a nonsurgical procedure to inject an anesthetic and/or medication into the epidural space of the spine. Conventional epidural needles include an elongated needle having a proximal end, a distal end and an axial hollow bore extending therethrough. The conventional epidural needle also includes a hub with a proximal end, a distal end and an open passageway, having an inside diameter therethrough, with the hub being attached to the elongated needle thereof so that the hollow bore of the elongated needle is in fluid communication and substantial axial alignment with the open passageway.

The conventional epidural needle has a flat blunt bevel at the outer end of the elongated needle that is designed to avoid puncturing the dura during insertion and to direct the direction of the catheter placement. Epidurals are used for regional anesthetic for pain management for labor and delivery and thoracic and abdominal surgeries.

In order to place an epidural needle, the anesthesiologist or injector will first use a large bore hypodermic needle to make an incision or hole in the skin. The anesthesiologist or injector will then place the hypodermic needle down. The injector then attempts to find the needle hole and threads the epidural needle through the incision or hole in the skin. Usually, the injector will use a hypodermic needle larger than necessary to create a large hole in the person's skin so that the insertion of the hypodermic needle through the needle hole is somewhat easier. Thus, the prior art method is a two-step process.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

An epidural needle assembly is disclosed for use in injecting medicine, anesthetic, etc. into a person or animal. The epidural needle assembly includes an epidural needle hub having a forward end and a rearward end and which has a first bore extending therethrough. An elongated epidural needle having a forward end and a rearward end, with a second bore, having rearward and forward ends, extending therethrough. The rearward end of the epidural needle is secured to the forward end of the epidural needle hub so as to extend forwardly therefrom with the rearward end of the second bore of the epidural needle being in communication with the first bore in the epidural needle hub. The forward end of the epidural needle is sharpened. The epidural needle hub has a docking portion at its forward end which extends forwardly therefrom.

The epidural needle assembly of this invention also includes an injection needle assembly comprising an injection needle hub, having a forward end and a rearward end, which has a bore extending therethrough with the bore of the injection needle hub having an enlarged bore portion at its rearward end. The injection needle assembly includes an elongated hollow injection needle having forward and rearward ends with the rearward end of the elongated hollow injection needle of the injection needle assembly being secured to the injection needle hub. The forward end of the elongated hollow injection needle has a sharp point with the rearward end of the elongated hollow injection needle being in communication with the bore of the injection needle hub. The injection needle assembly also includes a wing having inner and outer ends with the inner end of the wing being secured to the injection needle hub whereby the wing extends outwardly from the injection needle hub.

The injection needle hub is slidably mounted on the epidural needle whereby the epidural needle slidably extends through the rearward end of the injection needle hub, through the bore in the injection needle hub and through the injection needle. The injection needle hub and the injection needle are slidably movable with respect to the epidural needle between a first docked position and a second extended position. The rearward end of the injection needle hub receives the docking portion of the epidural needle hub to selectively maintain the injection needle hub and the injection needle in the first docked position. The forward end of the injection needle is positioned rearwardly of the forward end of the epidural needle when the injection needle hub and the injection needle are in the first docked position. The forward end of the injection needle is positioned forwardly of the forward end of the epidural needle when the injection needle hub and the injection needle are in the extended position.

In the preferred embodiment, the injection needle assembly includes a seal which is positioned in the injection needle hub and which has the epidural needle extending therethrough with the seal frictionally engaging the epidural needle to yieldably prevent the injection needle hub from slidably moving with respect to the epidural needle. In the preferred embodiment, a seal retainer is positioned in the injection needle hub to maintain the seal in the injection needle hub. In the preferred embodiment, the rearward end of the injection needle hub has radially spaced-apart slots formed therein.

The method of using the epidural needle assembly of this invention is also described.

It is therefore a principal object of the invention to provide an improved epidural needle assembly.

A further object of the invention is to provide an epidural needle assembly which eliminates the need for an injector having to utilize a hypodermic needle or the like to create an opening in a person or animal's skin prior to the insertion of the epidural needle.

A further object of the invention is to provide an epidural needle assembly which includes an injection needle assembly which is slidably mounted on the epidural needle.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Figure 1:
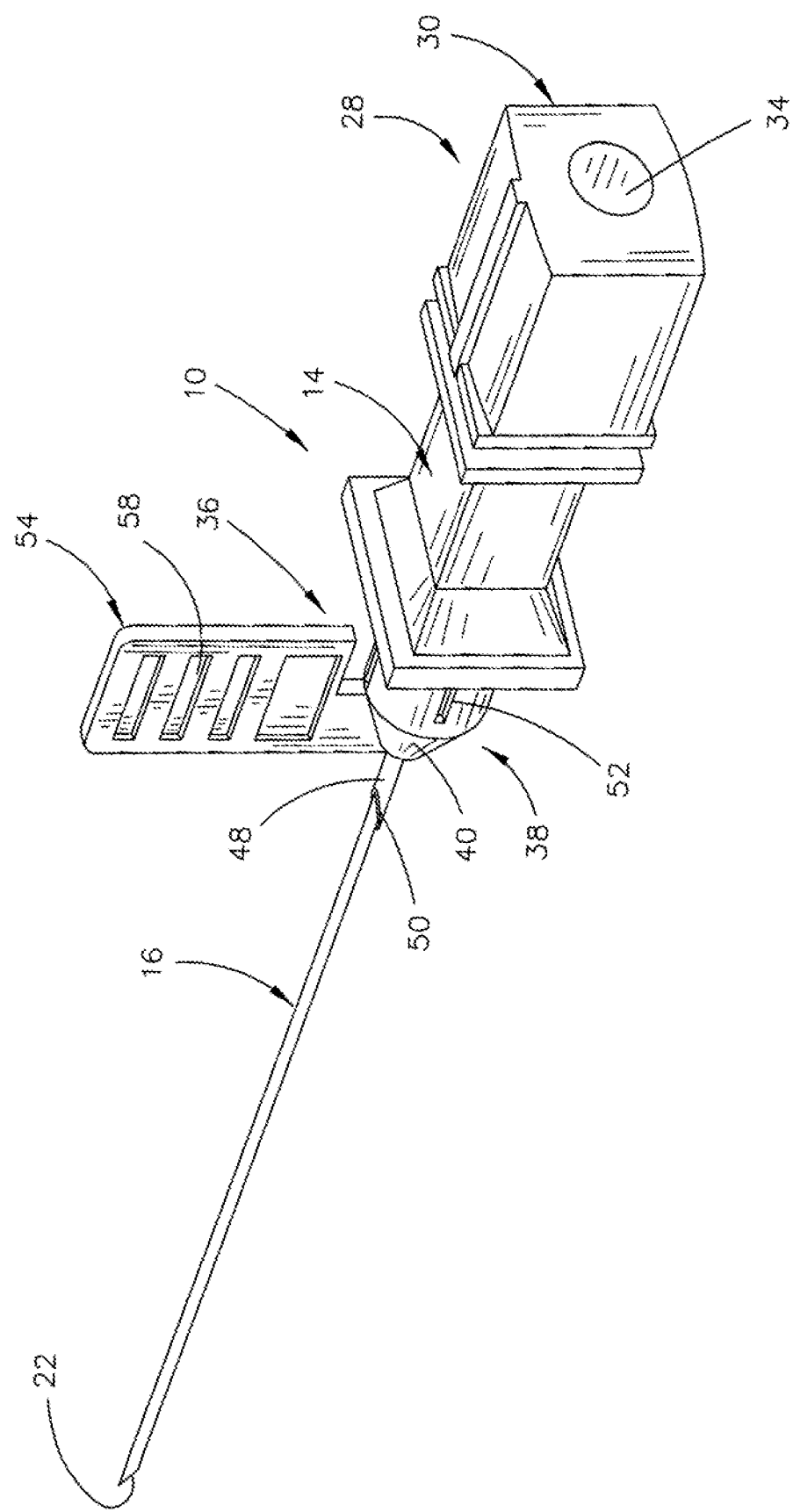
FIG. 1 is a rear perspective view of the epidural needle assembly of this invention.
Figure 2:
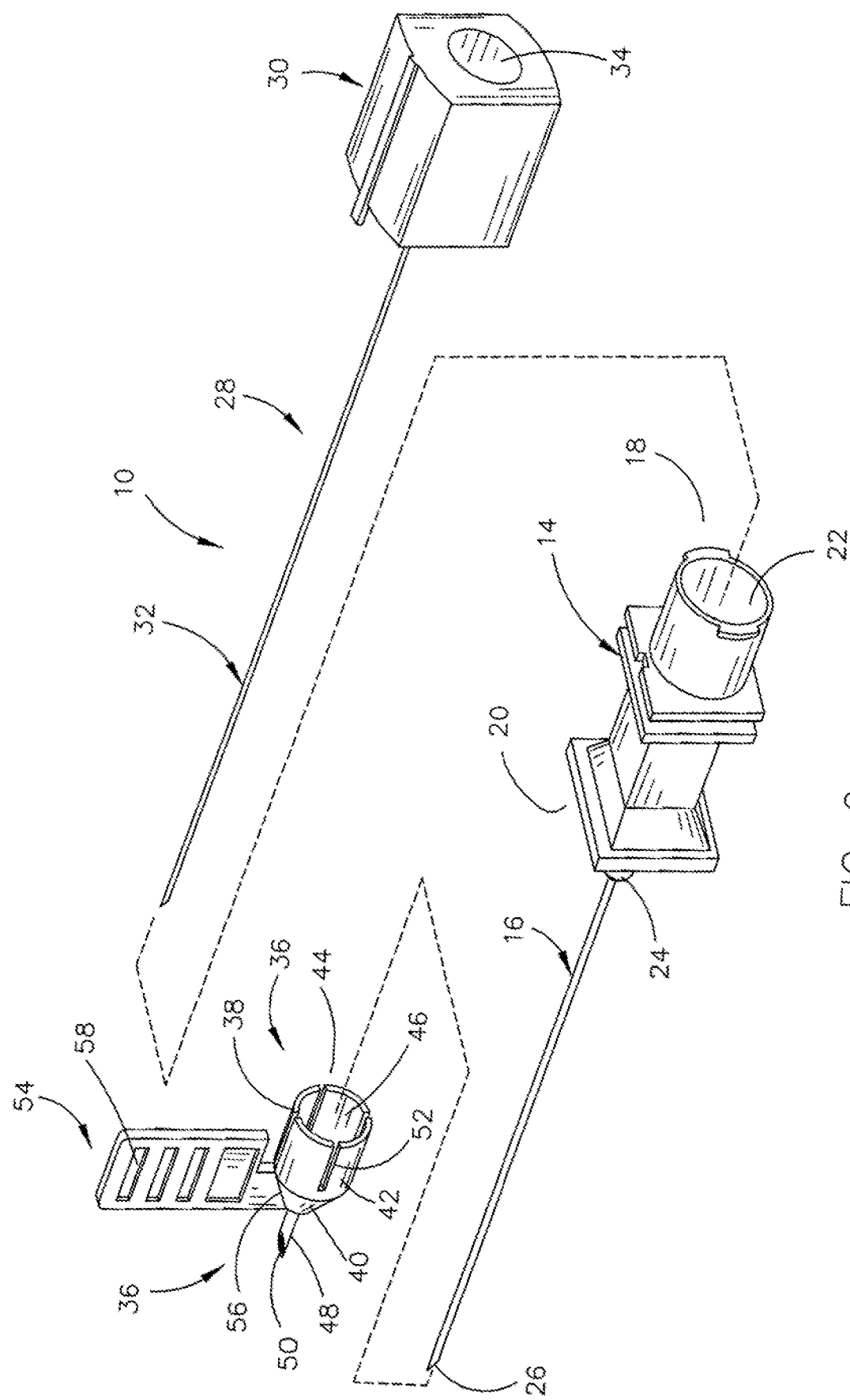
FIG. 2 is an exploded perspective view of the epidural needle assembly of this invention.
Figure 3:
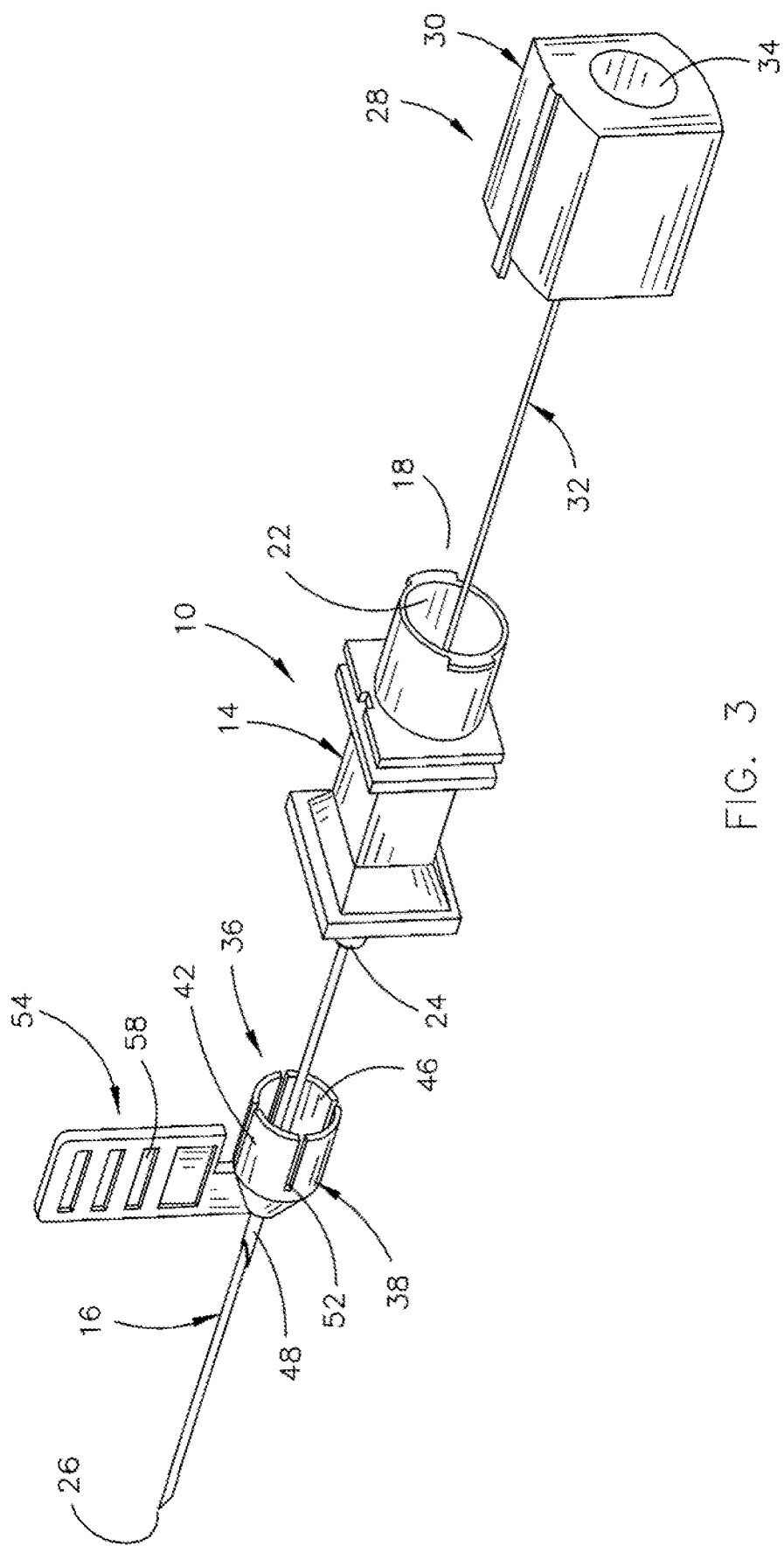
FIG. 3 is a perspective view of the epidural needle assembly which illustrates the injection needle assembly being slidably moved on the epidural needle and which the stylet of the epidural needle assembly has been partially removed therefrom.
Figure 4:
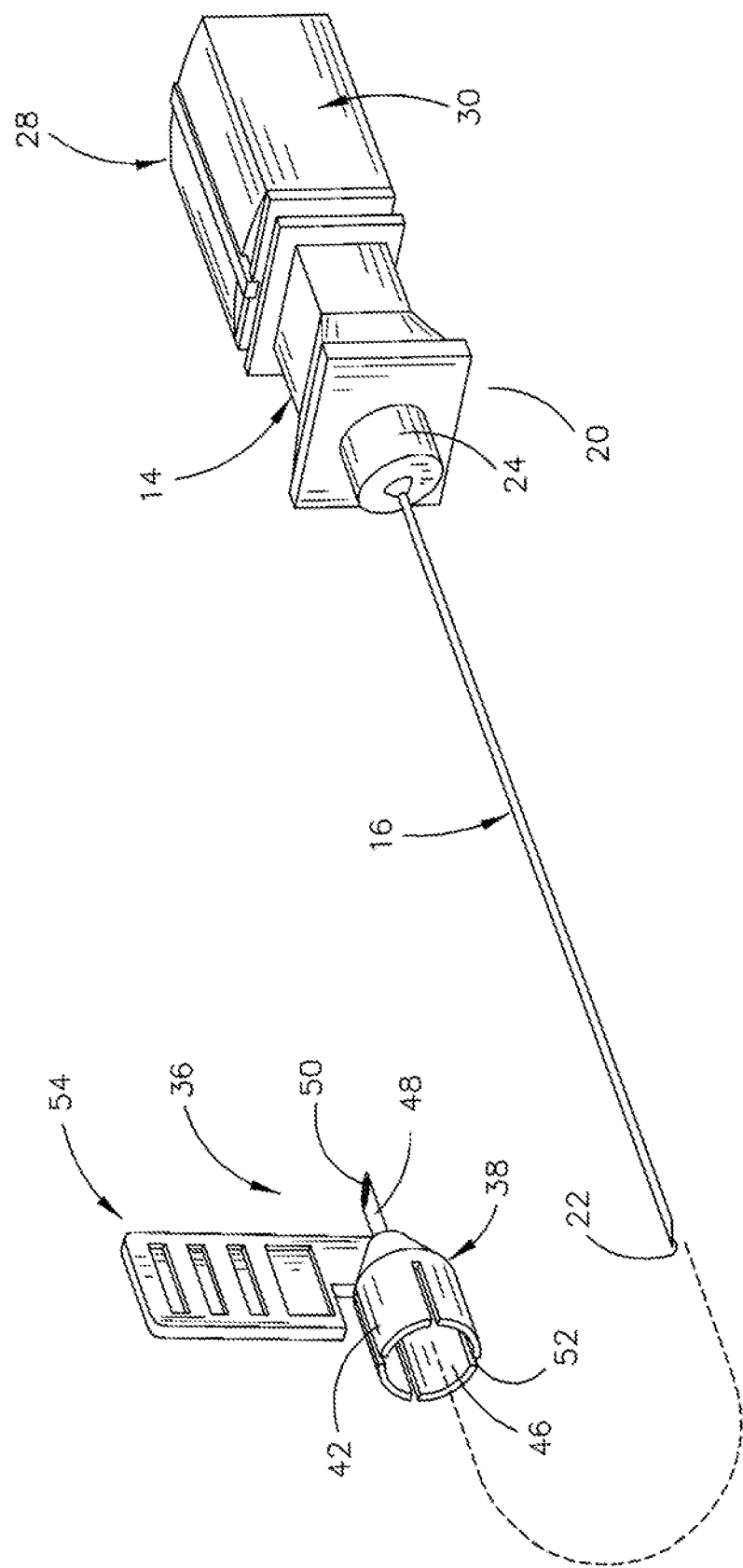
FIG. 4 is a perspective view which illustrates the injection needle assembly removed from the epidural needle.
Figure 5:
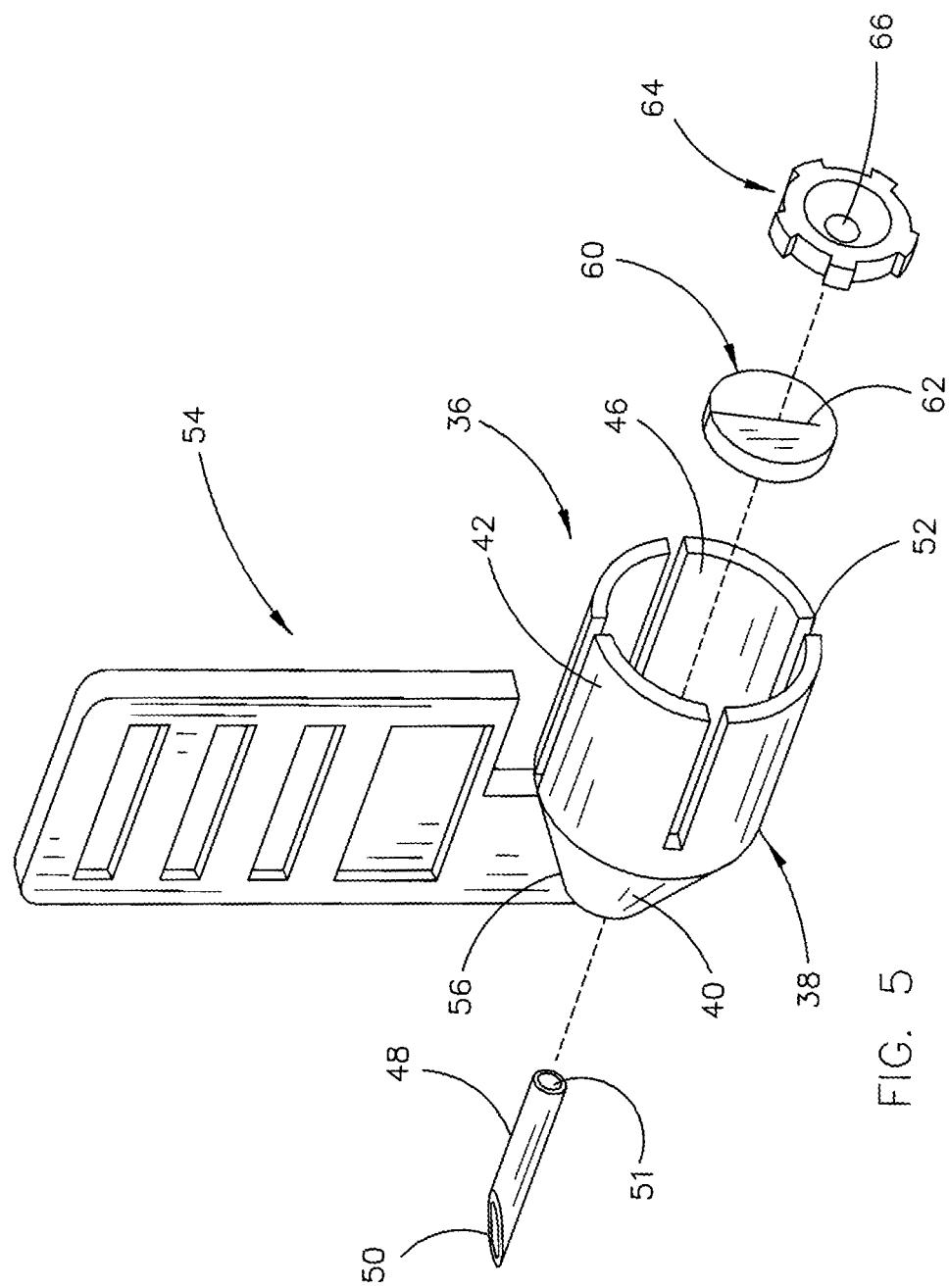
FIG. 5 is an exploded perspective view of the injection needle assembly.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The numeral 10 refers to the epidural needle assembly of this invention. Assembly 10 includes an epidural hub 14 and an elongated hollow needle 16 extending forwardly from hub 14. For purposes of description, hub 14 will be described as having a rearward end 18 and a forward end 20. Hub 14 has a bore 22 extending therethrough. A forwardly extending hollow docking portion 24 is provided at the forward end of hub 14, The rearward end of needle 16 is secured to the forward end of hub 14 so that the bore of needle 16 communicates with the bore 22 of hub 14. The forward end 26 of needle 16 is sharpened. Needle 16 may be straight or slightly curved.

In many cases, a stylet needle 28 is used with the epidural needle 16 to stiffen the needle 16 and to prevent tissue material or the like from passing into the interior of needle 16 when the needle 16 is inserted into a person or animal. Stylet needle 28 includes a hub 30 and a needle 32. Needle 32 is inserted into bore 22 of hub 14 and into the interior of needle 16 as seen in the drawings. When so inserted, the rearward end of hub 14 will be received by the forward end of bore 34 which extends through hub 30.

The numeral 36 refers to the injection needle assembly of this invention. Injection needle assembly 35 includes a hub 38 having a tapered forward end 40, an enlarged body portion 42 and a rearward end 44. Bore 46 extends through injection needle assembly 36 with the rearward end thereof being larger than the forward end thereof. A hollow injection needle 48 is secured to hub 38 and extends forwardly therefrom. The injection needle 48 has a sharpened forward end 50. The interior 51 of needle 48 communicates with the forward end of bore 46. Body portion 42 has a plurality of radially spaced-apart slots 52 formed therein. A wing 54 has its inner end 56 secured to hub 38 and extends outwardly therefrom. Wing 54 is preferably provided with indentions 58 formed therein to enable the wing 54 to be easily grasped.

Preferably, the injection needle assembly 36 includes a disc-shaped seal 60 positioned in bore 46 which has a slit 62 formed therein. Seal 60 is maintained in bore 46 by a retainer 64 having a central opening 66 formed therein. It is preferred that the injection needle 48 be 3 gauge sizes larger than the epidural needle 16.

The epidural needle assembly 10 is assembled and used as will now be described. Assuming that the epidural needle assembly 10 includes a stylet needle 28, the needle 32 of stylet needle 28 is inserted into the rearward end of bore 22 of hub 14 until the forward end of hub 30 of stylet needle 28 abuts hub 14 with the rearward end 18 of hub 14 being received by the forward end of bore 34 of hub 30 of stylet 28. The needle 32 will be positioned within needle 16. At that time, the forward end of needle 32 of stylet 28 will be positioned slightly inwardly of the forward end 26 of needle 16. The needle 32 stiffens the needle 16 and prevents tissue material from entering the forward end 26 of needle 16 as the needle 16 is inserted into a person or animal.

Figure 6:
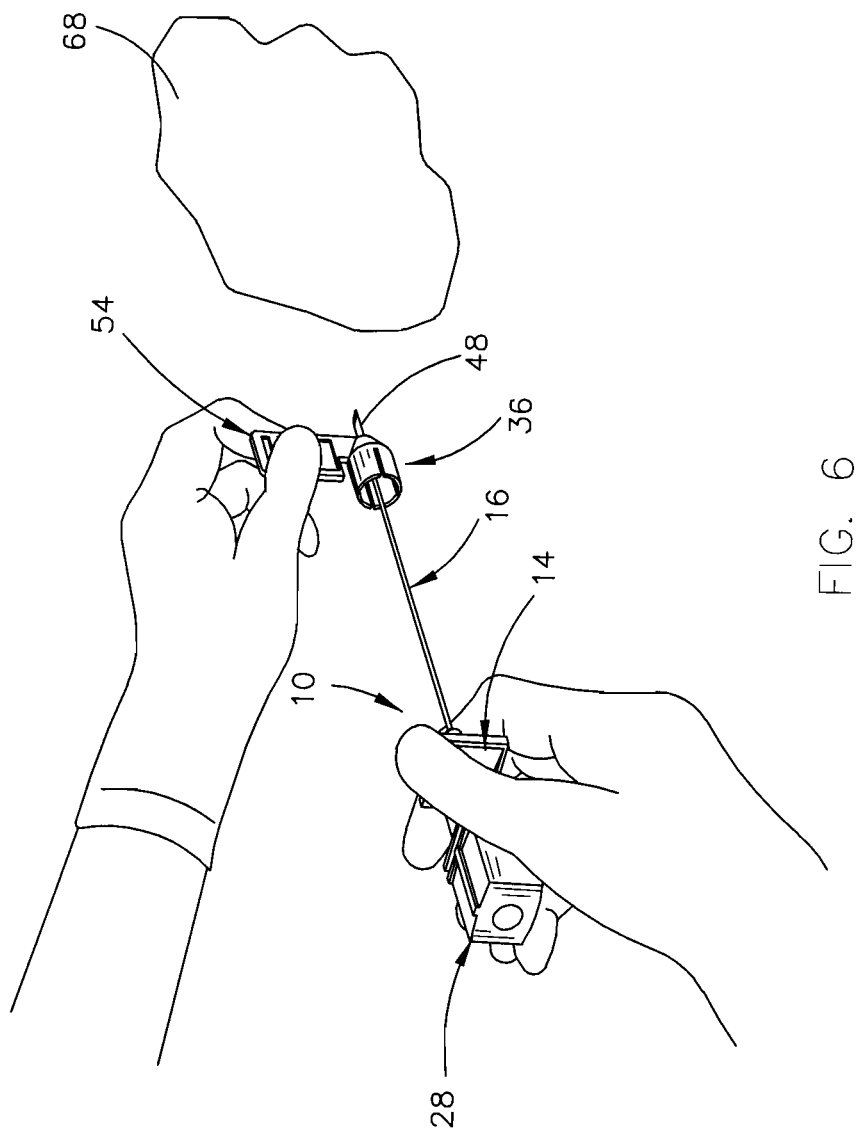
FIGS. 6-10 are perspective views which illustrate the manner which the epidural needle assembly of this invention is used to inject an anesthetic and/or medication into a person or animal.
Figure 7:
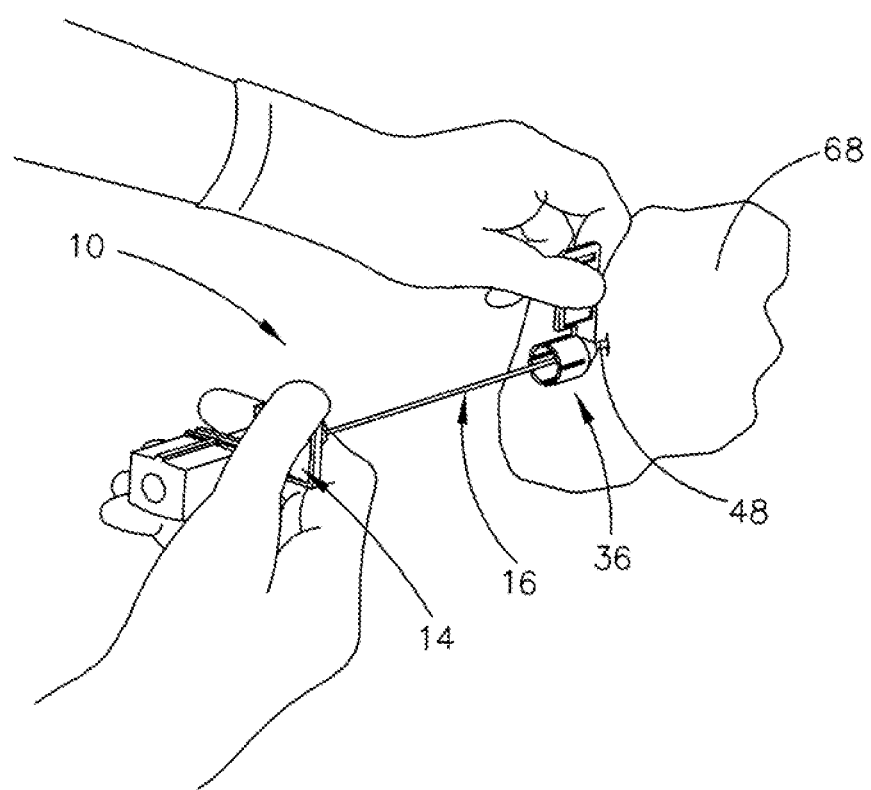

The injection needle assembly 36 will then be slipped onto needle 16 if not already done so. The needle 16 extends through bore 46 of hub 38 and into the needle 48. The injection needle assembly 36 will be slipped onto the needle 16 until the forward end 50 thereof is positioned just forwardly of the forward end 26 of needle 16 (FIG. 6). The epidural needle assembly 10 is then moved from the position of FIG. 6 to the position of FIG. 7 so that the sharpened forward end 50 of needle 48 pierces the skin 68 of the person or animal.

Figure 8:
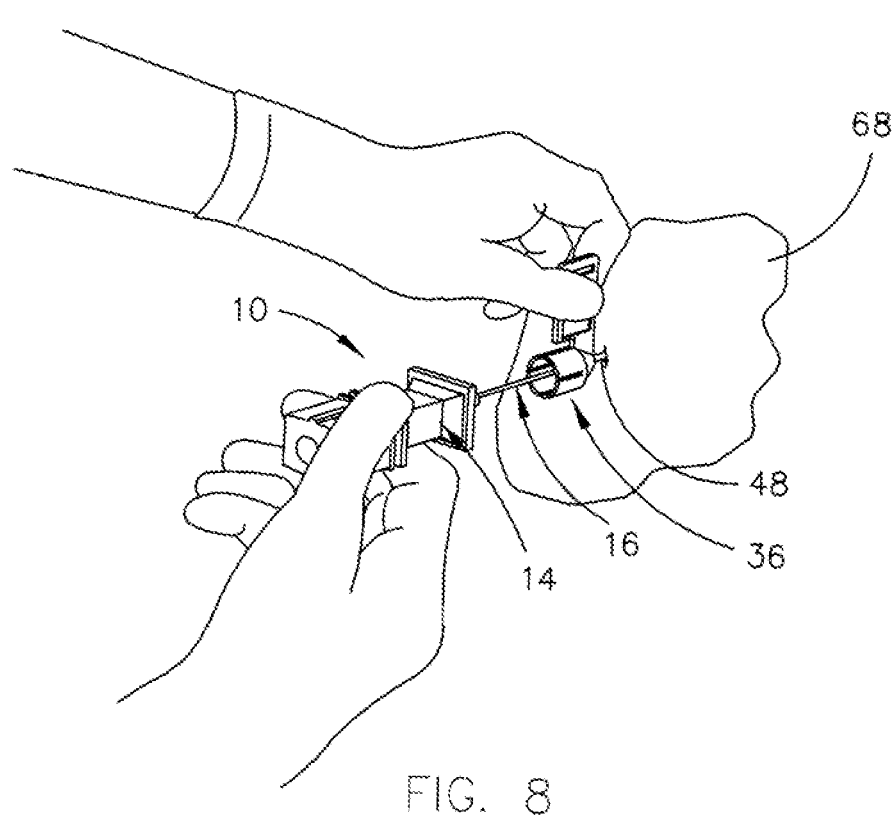
Figure 9:
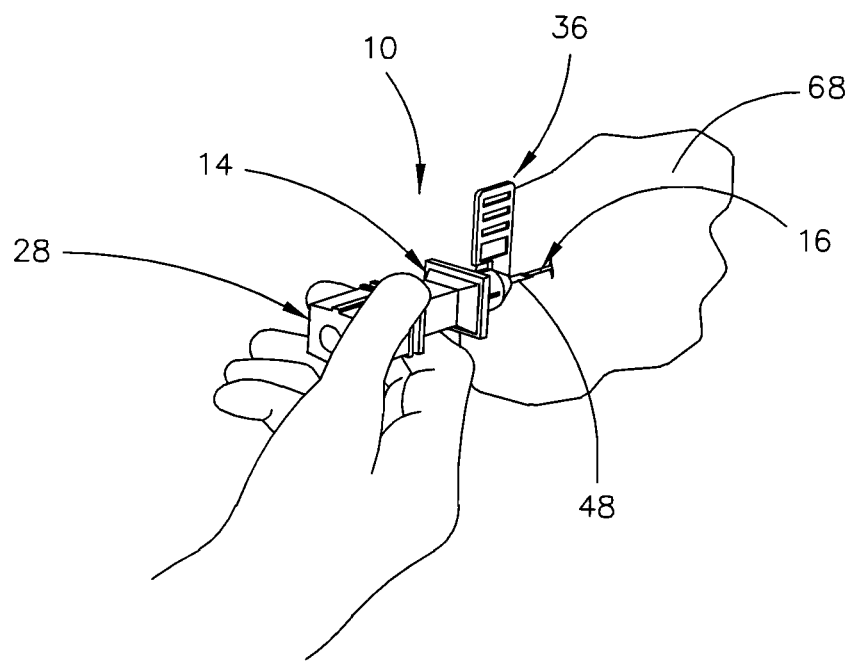
Figure 10:
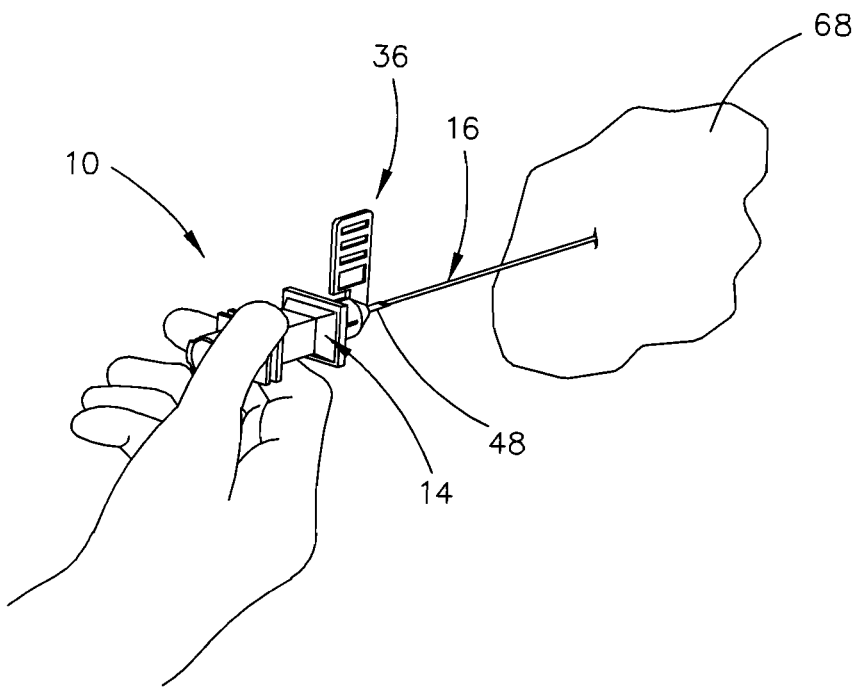

The needle 16 is then partially extended into the person or animal, while the injection needle assembly 36 is held in place (FIG. 8). The injection needle assembly 36 is then slidably moved rearwardly with respect to needle 16 to its docked position wherein the rearward end of body portion 42 is slipped onto the docking portion 26 of hub 14. The slots 52 on body portion 42 permit the rearward end of body portion 42 to deflect outwardly somewhat to permit the rearward end of body portion 42 to slip onto the docking portion 26. When the body portion 42 has been slipped onto the docking portion 26, the frictional engagement of the body portion 42 with the docking portion 26 causes the body portion 42 to be yieldably held onto the docking portion 26.

The needle 16 is then extended into the person or animal until the proper depth has been reached. If the assembly includes the stylet needle 28, the stylet needle 28 is then removed from the assembly. A syringe or other medical device is then coupled to the hub 14 so that medicine or anesthetic may be injected into the person or animal. When the medicine or anesthetic has been injected into the person or animal, the epidural needle assembly 10 is moved away from the person or animal to remove the needle 16 from the person or animal.

Although it is preferred that the invention includes a docking portion 26 at the forward end of hub 14, the docking portion may be omitted in some cases. Although it is preferred that the wing 54 be utilized, there are some cases wherein the wing 54 may be omitted.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

We claim:

1. An epidural needle assembly, comprising:
an epidural needle hub having a forward end and a rearward end;
said epidural needle hub having a first bore extending therethrough;
an elongated hollow epidural needle having a forward end and a rearward end;
said rearward end of said elongated hollow epidural needle being secured to said forward end of said epidural needle hub so as to extend forwardly therefrom;
said rearward end of said elongated hollow epidural needle being in communication with said first bore in said epidural needle hub;
said forward end of said elongated hollow epidural needle being sharpened;
an injection needle assembly including an injection needle hub having a forward end, an enlarged body portion and a rearward end;
said enlarged body portion of said injection needle hub having a forward end and a rearward end;
a bore extending through said injection needle hub with said bore having a forward end and a rearward end with said rearward end of said bore having a greater diameter than said forward end thereof;
said injection needle assembly including an elongated hollow injection needle having a forward end and a rearward end;
said rearward end of said elongated hollow injection needle being secured to said injection needle hub;
said forward end of said elongated hollow injection needle having a sharp point;
said rearward end of said elongated hollow injection needle being in communication with said bore of said injection needle hub;
said hollow injection needle having a diameter which is larger than the diameter of said elongated hollow epidural needle;
said injection needle hub being slidably mounted on said elongated hollow epidural needle whereby said elongated hollow epidural needle slidably extends through said rearward end of said injection needle hub, through said bore in said injection needle hub and through said hollow injection needle;
said injection needle hub and said hollow injection needle being slidably movable with respect to said elongated hollow epidural needle and said epidural needle hub between a first retracted position and a second extended position;
said injection needle hub and said hollow injection needle being positioned on said elongated hollow epidural needle when said injection needle hub and said elongated hollow injection needle are in said retractable and extended positions;
said forward end of said hollow injection needle being positioned rearwardly of said forward end of said elongated hollow epidural needle when said injection needle hub and said hollow injection needle are in said first retracted position;
said forward end of said hollow injection needle being positioned forwardly of said forward end of said elongated hollow epidural needle when said injection needle hub and said hollow injection needle are in said second extended position to enable said forward end of said hollow injection needle to be first inserted into various parts of a person or animal, without said forward end of said elongated hollow epidural needle penetrating the person or animal, and to enable said forward end of said elongated hollow epidural needle to subsequently pass through said bore of said injection needle hub and said hollow injection needle into the person or animal while said injection needle hub and said hollow injection needle are in said second extended position; and
said rearward end of said enlarged body portion of said injection needle hub being in frictional contact with said forward end of said epidural needle hub only when said injection needle hub and said hollow injection needle are in said first retracted position to maintain said injection needle hub and said elongated hollow injection needle in said first retracted position.

2. An epidural needle assembly, comprising:
an epidural needle hub having a forward end and a rearward end;
said epidural needle hub having a cylindrical docking portion at said forward end of said epidural needle hub, the cylindrical docking portion extending forwardly therefrom;
said epidural needle hub having a first bore extending therethrough;
an elongated hollow epidural needle having a forward end and a rearward end;
said rearward end of said elongated hollow epidural needle being secured to said forward end of said epidural needle hub so as to extend forwardly therefrom;
said rearward end of said elongated hollow epidural needle being in communication with said first bore in said epidural needle hub;
said forward end of said elongated hollow epidural needle being sharpened;
an injection needle assembly including an injection needle hub having a forward end, an enlarged body portion and a rearward end;
said enlarged body portion having a forward end and a rearward end;
a bore extending through said injection needle hub with said bore having forward end and a rearward end with said rearward end of said bore having a greater diameter than said forward end thereof;
said injection needle assembly including an elongated hollow injection needle having a forward end and a rearward end;
said rearward end of said elongated hollow injection needle being secured said injection needle hub;
said forward end of said elongated hollow injection needle having a sharp point;
said rearward end of said elongated hollow injection needle being in communication with said bore of said injection needle hub;
said injection needle hub being slidably mounted on said elongated hollow epidural needle whereby said elongated hollow epidural needle slidably extends through said rearward end of said injection needle hub, through said bore in said injection needle hub and through said hollow injection needle;
said injection needle hub and said hollow injection needle being slidably movable with respect to said elongated hollow epidural needle and said epidural needle hub between a first retracted position and a second extended position;

said injection needle hub and said hollow injection needle being positioned on said elongated hollow epidural needle when said injection needle hub and said elongated hollow injection needle are in said retractable and extended positions;

said forward end of said hollow injection needle being positioned rearwardly of said forward end of said elongated hollow epidural needle when said injection needle hub and said hollow injection needle are in said first retracted position;

said forward end of said hollow injection needle being positioned forwardly of said forward end of said elongated hollow epidural needle when said injection needle hub and said hollow injection needle are in said second extended position to enable said forward end of said hollow injection needle to be first inserted into various parts of a person or animal, without said forward end of said elongated hollow epidural needle penetrating the person or animal, and to enable said forward end of said elongated hollow epidural needle to subsequently pass through said bore of said injection needle hub and said hollow injection needle into the person or animal while said injection needle hub and said hollow injection needle are in said second extended position;

said rearward end of said body portion of said injection needle hub having a plurality of radially spaced-apart slots formed therein which extend forwardly from said rearward end of said body portion of said injection needle hub;

said injection needle assembly being selectively slidably moved rearwardly with regard to said epidural needle to a docked position wherein said rearward end of said body portion is slipped onto said cylindrical docking portion with said slots on said body portion permitting said rearward end of said body portion to deflect outwardly to permit said rearward end of said body portion to slip onto and embrace said cylindrical docking portion; and said body portion being in frictional contact with said cylindrical docking portion causing said body portion to be held onto said cylindrical docking portion only when said infection needle hub and said hollow injection needle are in said docked position.

\* \* \* \* \*